US008460217B2

(12) United States Patent
Shakiba

(10) Patent No.: US 8,460,217 B2
(45) Date of Patent: Jun. 11, 2013

(54) ELECTRONIC PELVIC ORGAN PROLAPSE QUANTIFICATION SYSTEM

(76) Inventor: Khashayar Shakiba, Ridgewood, NJ (US)

( * ) Notice: Subject to any disclaimer, the term of this patent is extended or adjusted under 35 U.S.C. 154(b) by 133 days.

(21) Appl. No.: 12/893,626

(22) Filed: Sep. 29, 2010

(65) Prior Publication Data
US 2011/0077500 A1    Mar. 31, 2011

Related U.S. Application Data

(60) Provisional application No. 61/246,607, filed on Sep. 29, 2009.

(51) Int. Cl.
*A61B 5/103* (2006.01)
*A61B 5/11* (2006.01)
*A61F 6/08* (2006.01)

(52) U.S. Cl.
USPC ............. 600/591; 600/30; 600/587; 600/595; 128/834

(58) Field of Classification Search
USPC ...................... 128/834; 600/30, 587, 591, 595
See application file for complete search history.

(56) References Cited

U.S. PATENT DOCUMENTS

| | | | | |
|---|---|---|---|---|
| 4,669,478 A * | 6/1987 | Robertson | ................... | 600/300 |
| 4,873,990 A * | 10/1989 | Holmes et al. | ................ | 600/561 |
| 5,167,237 A * | 12/1992 | Rabin et al. | .................... | 600/561 |
| 6,039,701 A * | 3/2000 | Sliwa et al. | .................... | 600/588 |
| 6,063,045 A * | 5/2000 | Wax et al. | ...................... | 600/591 |
| 6,080,118 A * | 6/2000 | Blythe | .......................... | 600/591 |
| 6,217,529 B1 * | 4/2001 | Wax et al. | ..................... | 600/591 |
| 6,468,232 B1 * | 10/2002 | Ashton-Miller et al. | ..... | 600/591 |
| 6,547,748 B1 * | 4/2003 | Shine | ............................ | 600/588 |
| 6,905,471 B2 * | 6/2005 | Leivseth et al. | ............... | 600/591 |
| 7,615,014 B2 * | 11/2009 | Omata et al. | .................. | 600/587 |
| 7,628,744 B2 * | 12/2009 | Hoffman et al. | .............. | 482/148 |
| 7,645,220 B2 * | 1/2010 | Hoffman et al. | .............. | 482/148 |
| 7,713,216 B2 * | 5/2010 | Dubey et al. | .................. | 600/588 |
| 7,955,241 B2 * | 6/2011 | Hoffman et al. | .............. | 482/148 |
| 8,147,429 B2 * | 4/2012 | Mittal et al. | .................. | 600/591 |
| 8,412,318 B2 * | 4/2013 | Edwards et al. | ................ | 604/21 |
| 2004/0122341 A1 * | 6/2004 | Walsh et al. | ................... | 600/591 |
| 2006/0020297 A1 * | 1/2006 | Gerber et al. | ................... | 607/39 |
| 2006/0064038 A1 * | 3/2006 | Omata et al. | .................. | 600/587 |
| 2007/0156068 A1 * | 7/2007 | Dubey et al. | .................. | 600/588 |
| 2007/0185417 A1 * | 8/2007 | Mittal et al. | .................. | 600/591 |
| 2008/0077053 A1 * | 3/2008 | Epstein et al. | ............... | 600/591 |
| 2010/0076255 A1 * | 3/2010 | Robertson et al. | .............. | 600/30 |

FOREIGN PATENT DOCUMENTS
CA         2290898 A1 *    3/2001

* cited by examiner

*Primary Examiner* — Sean Dougherty
(74) *Attorney, Agent, or Firm* — Fox Rothschild LLP; Gerard P. Norton; Jianming Jimmy Hao

(57) ABSTRACT

Systems and related methods for measuring pelvic organ prolapse are disclosed. A plurality of positioning devices, such as RFID tags, ultrasound reflectors or magnetic field sensors, which may be active or passive, and which are preferably disposable, are set at predetermined positions within the patient and their relative positions recorded with one or more corresponding external receiving devices fixed to the patient while the patient is in a relaxed state. The patient is then instructed to perform an action (such as a valsalva maneuver) that causes the positioning devices to move and their movement relative to their initial recorded positions is measured.

8 Claims, 9 Drawing Sheets

ELECTRONIC PELVIC ORGAN PROLAPSE QUANTIFICATION SYSTEM

CROSS-REFERENCE TO RELATED APPLICATIONS

This application claims the benefit of U.S. Provisional Application 61/246,607, filed on Sep. 29, 2009, the teachings of which is incorporated herein by reference.

FIELD OF THE INVENTION

The present invention relates generally to devices and methods for measuring pelvic organ prolapse.

BACKGROUND OF THE INVENTION

Pelvic organ prolapse is common. In the United States, 24 percent of women have some type of pelvic floor disorder. See Nygaard I; Barber M D; Burgio K L; Kenton K; Meikle S; Schaffer J; Spino C; Whitehead W E; Wu J; Brody D J; Prevalence of Symptomatic Pelvic Floor Disorders in US Women; JAMA; 2008 Sep. 17; 300(11):1311-6. The Women's Health Initiative reported 34 percent of women had anterior vaginal wall prolapse, 19 percent had posterior vaginal wall prolapse, and 14 percent had uterine prolapse on physical examination. See Hendrix S L; Clark A; Nygaard I; Aragaki A; Barnabei V; McTiernan A; Pelvic Organ Prolapse in the Women's Health Initiative: Gravity and Gravidity; Am J Obstet Gynecol 2002 June; 186(6):1160-6. Population-based surveys have found that 4 to 10 percent of women report symptoms of pelvic organ prolapse. See Bradley C S; Nygaard I E; Vaginal Wall Descensus and Pelvic Floor Symptoms in Older Women; Obstet Gynecol. 2005 October; 106(4):759-66. Rortveit G; Brown J S; Thom D H; Van Den Eeden S K; Creasman J M; Subak L L; Symptomatic Pelvic Organ Prolapse: Prevalence and Risk Factors in a Population-Based, Racially Diverse Cohort; Obstet Gynecol. 2007 June; 109(6):1396-1403. Tegerstedt G; Maehle-Schmidt M; Nyren O; Hammarstrom M; Prevalence of Symptomatic Pelvic Organ Prolapse in a Swedish Population; Int Urogynecol J Pelvic Floor Dysfunct; 2005 November-December; 16(6): 497-503; Epub 2005 Jun. 29.

Women are living longer and want to maintain their physique and capacity for sexual function well beyond menopause. Few maladies are more disruptive to these goals than pelvic organ prolapse, which is responsible for more than 200,000 surgical repair procedures each year (22.7 per 10,000 women) at an annual cost of more than $1 billion. See Boyles S H; Weber A M; Meyn L; Procedures for Pelvic Organ Prolapse in the United States, 1979-1997; Am J Obstet Gynecol 2003 January; 188(1):108-15. Subak L L; Waetjen L E; van den Eeden S; Thom D H; Vittinghoff E; Brown J S; Cost of Pelvic Organ Prolapse Surgery in the United States; Obstet Gynecol 2001 October; 98(4):646-51. Despite its prevalence, there is unfortunately no accurate, site-specific system for describing, quantifying, and staging pelvic support in women in order to provide a standardized means for documenting, comparing, and communicating clinical findings with proven interobserver and intraobserver reliability.

The most accurate system available as of today is the Pelvic Organ Prolapse Quantification system (POP-Q), which refers to a totally objective, examiner dependent, and complicated site-specific system for describing, quantifying, and staging pelvic support in women. See Bump, R C, Mattiasson, A, Bo, K, et al.; The Standardization of Terminology of Female Pelvic Organ Prolapse and Pelvic Floor Dysfunction; Am J Obstet Gynecol 1996; 175:10. The POP-Q system is approved by the International Continence Society (ICS), the American Urogynecologic Society (AUGS), and the Society of Gynecologic Surgeons for the description of female pelvic organ prolapse. It is the most common system used by gynecologists, although other systems have been devised. See Hall A F; Theofrastous J P; Cundiff G W; Harris R L; Hamilton L F; Swift S E; Bump R C; Interobserver and Intraobserver Reliability of the Proposed International Continence Society, Society of Gynecologic Surgeons, and American Urogynecologic Society Pelvic Organ Prolapse Classification System; Am J Obstet Gynecol 1996 December; 175(6):1467-70; discussion 1470-1.

The POP-Q system suffers from the following weaknesses:

1) Difficulty of performance of the measurement secondary to patient body habitus and distorted anatomy.

2) It is completely objective: POP-Q measurements are totally operator dependant and therefore not very accurate. Unfortunately, most gynecologists worldwide lack an accurate technique for the measurement of pelvic organ prolapses.

3) Even in well trained operators the measurement of pelvic organ prolapse remains primarily based on objective measurements, and the operators tend to measure and score the numbers based on visual estimations rather than being based on real instrumental measurements.

4) the POP-Q system is unable to assess and quantify pelvic organ prolapse in the standing position. This is a big disadvantage given the fact that the worst occurrences of prolapse happen while in the standing position.

5) Although POP-Q is the most common method of describing pelvic organ prolapse used in research or peer-reviewed literature, the staging system was not cited or a non-standardized staging system was used in more than half of the studies. See Muir T W; Stepp K J; Barber M D; Adoption of the Pelvic Organ Prolapse Quantification System in Peer-reviewed Literature; Am J Obstet Gynecol 2003 December; 189(6):1632-5; discussion 1635-6. This illustrates the lack of reliability of the POP-Q system even for research purposes.

6) An accurate performance of POP-Q is time consuming and therefore does not make economic sense for many physicians.

In summary, performance of an accurate POP-Q exam in a gynecology office is very time consuming, difficult, objective, and overall not very accurate and reproducible. International surveys show that only 40.2% of International Continence Society (ICS) and American Urogynecology Society (AUGS) members routinely use the POP-Q system in their clinical practice. The results highlight some of the concerns regarding the complex nature of the system and its acceptance and use by specialists worldwide. It also suggests the need for a simplified version of the classification system that is user-friendly and that can be adopted by all practitioners. See Auwad W; Freeman R M; Swift S; Is the Pelvic Organ Prolapse Quantification System (POPQ) Being Used? A Survey of Members of the International Continence Society (ICS) and the American Urogynecologic Society (AUGS); Int Urogynecol J Pelvic Floor Dysfunction. 2004 September-October; 15(5):324-7; Epub 2004 May 18. The use of the POP-Q system is certainly much lower than 40% among typical gynecologists without specific urogynecologic training.

Accordingly, there is an immediate need for improved methods and devices for measuring pelvic organ prolapse.

SUMMARY OF THE INVENTION

In one aspect, a method for determining pelvic organ prolapse is disclosed that employs internally positioned positioning devices and related external equipment to measure the movement of the positioning devices during a pelvic exam. Related systems are also disclosed.

In various embodiments, an electromagnetic, ultrasound or radio-frequency identification (RFID) based system for precisely and electronically measuring and quantifying the degree of female pelvic organ prolapse is disclosed. The system is capable of accurately and site-specifically describing, quantifying, and staging pelvic support in women in order to provide a standardized means for documenting, comparing, and communicating clinical findings with proven interobserver and intraobserver reliability, prior and after surgical treatment. The system includes positioning devices that may placed internally within the patient and receiver equipment that is capable of determining the positions, relative positions or movements of the positioning devices within the patient. The positioning devices may be active (such as by broadcasting an electromagnetic signal) or passive, and are preferably disposable.

DETAILED DESCRIPTION

Figure 1:
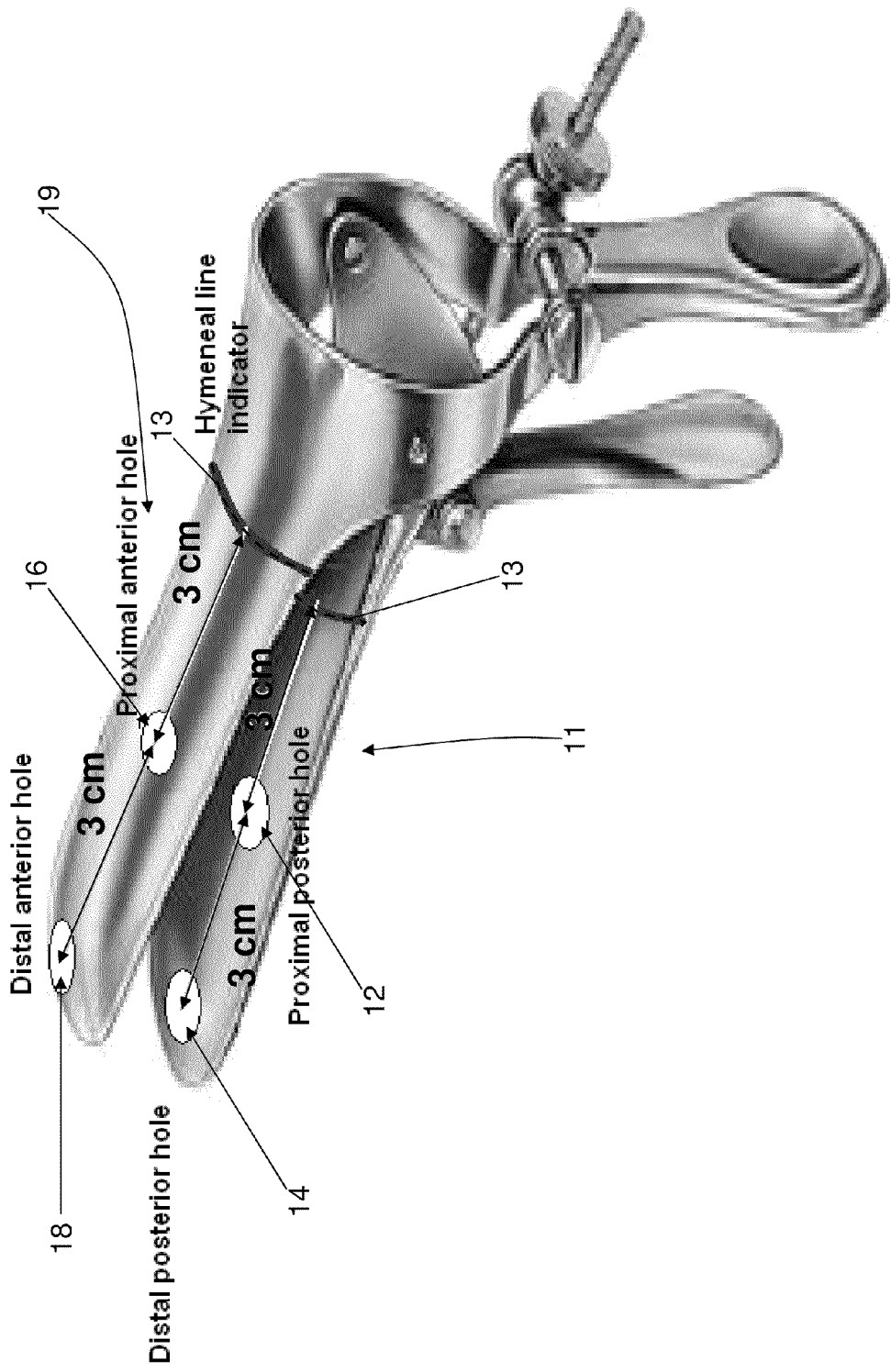
FIG. 1 illustrates an embodiment speculum designed for an embodiment modified POP-Q system.

As detailed above, there is a need for an electronic system as described herein, which is capable of accurately and site-specifically describing, quantifying, and staging pelvic support in women in order to provide a standardized means for documenting, comparing, and communicating clinical findings with proven interobserver and intraobserver reliability.

Furthermore, embodiment methods, devices and systems enable the clinician to assess pelvic support defects in a variety of positions, including standing and sitting. Also, various embodiments enable the clinician to have an evaluation tool for long term follow-up after any reconstructive surgery. This post-operative evaluation can precisely identify and compare the failure rate of different types of procedures with proven interobserver and intraobserver reliability. This opens a wide area of research in order to find the best possible reconstructive surgery and hence to provide the best possible care for women.

The fixed point of reference for preferred embodiment modified POP-Q measurements is the hymen. In such embodiments, a plurality of points, and preferably six points (two on the anterior vaginal wall, two on the superior vagina, and two on the posterior vaginal wall) are measured with reference to the plane of the hymen. Positioning devices are then set at these points for measurement purposes. Any suitable device may be used as a positioning device to effect the measurements as set forth in the following, and each positioning device is used to obtain corresponding positioning information, as discussed below. In preferred embodiments the positioning devices are any suitable types of electromagnetic sensors, RFID tags or ultrasonic reflectors. However, it will be appreciated that any suitable device may be used from which suitable positioning information may be obtained. Suitable positioning information may include information that indicates the actual position of each device within the patient, information that indicates relative movement of the devices with respect to each other within the patient, information that provides displacement information of the device within the patient, movement of the device with respect to an external reference, combinations thereof and so forth. Typically, positioning information will have X, Y and Z spatial components, whether absolute (such as in reference to a fixed point in the exam room or on the patient) or relative (such as displacements from a position or with respect to another positioning device). Such positioning devices may be active or passive. In preferred embodiments the devices are passive, and in particularly preferred embodiments the devices are also disposable. External to the patient are one or more corresponding receivers that use the positioning devices to generate the positioning information. As discussed in the following, a positioning receiver may also include a transmitting component, which may be physically part of the receiver or a discrete unit. The external positioning receiver or receivers may include, for example, processing equipment and related software, and a screen to present, for example, the positioning information or data related thereto and diagnosis information derived therefrom.

In an embodiment diagnostic method, positioning devices are removably attached to the interior walls of the vaginal cavity as predetermined positions using any suitable method, such as adhesives, clamps or the like. These positions are discussed in the following. Although specific distances are discussed in the following, it will be understood that variations from these distances are possible based upon, for example, the specific anatomy of the patient be examined. Hence, these distances are approximate, but the range of such variations should be understood by one of ordinary skill in the art after reading the following disclosure in light of the intended objectives.

Figure 2:
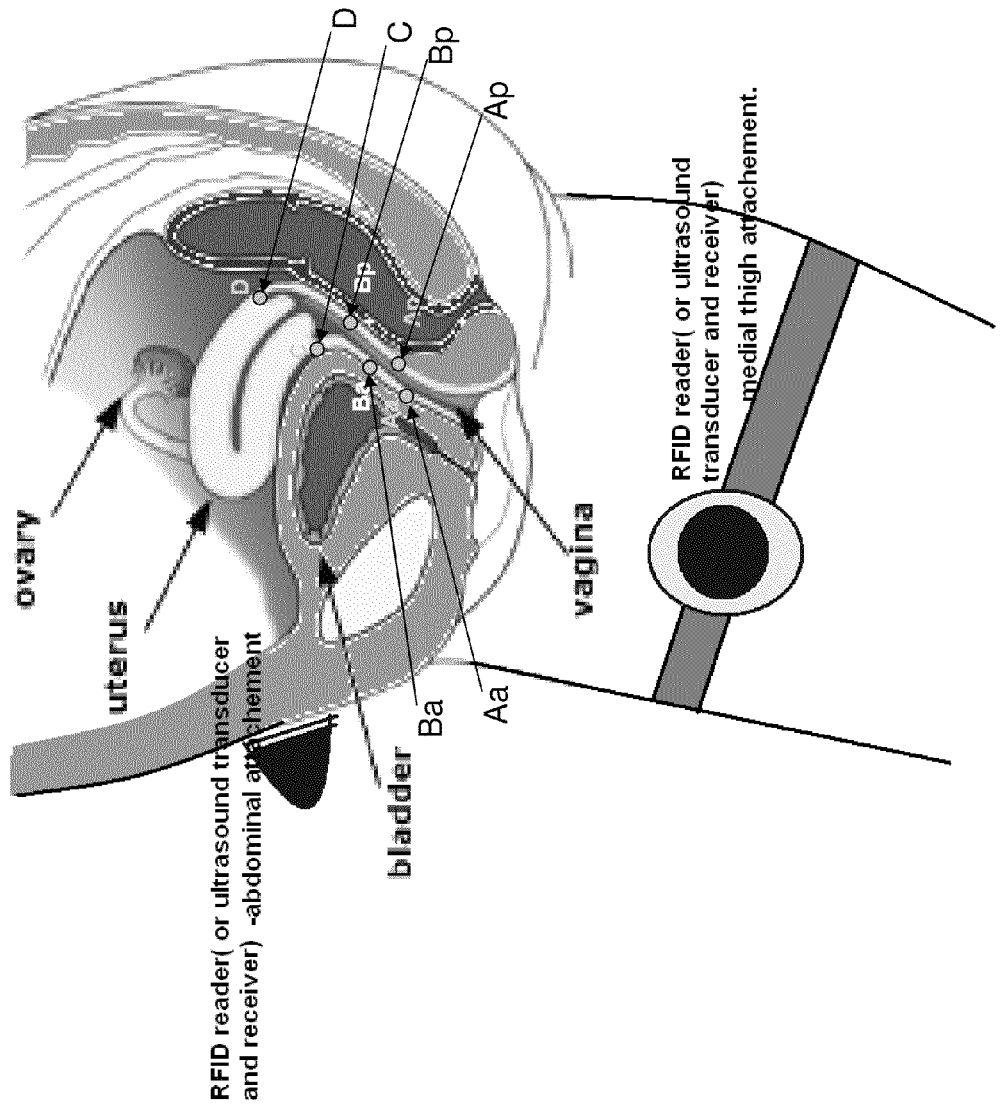
FIG. 2 is a side view of positioning devices placed on the vaginal epithelium according to an embodiment mapping system.

As shown in FIG. 2, two points are located on the anterior vaginal wall:

Point Aa is located at the midline of the anterior vaginal wall, preferably about 3 cm proximal to the external urethral meatus or hymen. Point Aa corresponds approximately or exactly to the urethrovesical junction.

Point Ba is preferably about 3 cm proximal to point Aa, and approximately or exactly reflects halfway between the urethrovesical junction and anterior vaginal formix. In a woman that has undergone a total post-hysterectomy, if the vagina is short and the distance between point Aa and the vaginal cuff is less than 5 cm, point Ba may be disregarded and there may be no need for positioning device placement at point Ba.

Two points are located in the superior vagina:

Point C is the most distal (i.e., most dependent) edge of the cervix or the leading edge of the vaginal cuff after hysterectomy.

Point D is the deepest point of the posterior formix in a woman who still has a cervix. It is preferably located where the uterosacral ligaments attach to the posterior cervix. Measuring this point distinguishes between suspensory failure of the uterosacral-cardinal ligament complex and cervical elongation: if point C is significantly more positive than point D (e.g., greater than 4 cm), the cervix is elongated. In a woman with a status post-hysterectomy, point D may be disregarded and placement of a positioning device on point C may be sufficient.

Two points are measured on the posterior vaginal wall, analogous to the two points on the anterior wall.

Point Ap is located in the midline of the posterior vaginal wall, and is preferably about 3 cm proximal to the hymen.

Point Bp is preferably about 3 cm proximal to point Ap, and approximately reflects a deeper defect like enterocele. In a woman with a total post-hysterectomy, if the vagina is short and the distance between point Ap and the vaginal cuff is less than 5 cm, point Bp may be disregarded and there is thus no need for positioning device placement on this point.

Two measurements give a frontal view of prolapse from the perspective of an examination in the lithotomy position. These measurements complement points determined in the sagittal view:

The genital hiatus (gh) is measured from the middle of the external urethral meatus to the posterior midline hymen. If the location of the hymen is obscured by a band of skin (usually from surgery or episiotomy repair), the firm tissue of the perineal body may be the posterior margin of this measurement.

The perineal body (pb) is measured from the posterior margin of the genital hiatus to the midanal opening.

Finally, the total vaginal length (TVL) is measured as the greatest depth of the vagina when point C or D is reduced completely to its normal position.

Method of the Placement of Positioning Devices Inside the Vagina

A special speculum and applicator may be designed to facilitate the precise placement of the positioning devices, such as ultrasonic reflectors, RFID tags or the like, on the vaginal epithelium in a safe and sterile manner. FIG. 1 illustrates an embodiment speculum 10. This speculum 10 is preferably made from a transparent plastic material, which may be disposable. The speculum 10 includes two blades 11, 19, and each blade 11, 19 has two holes 12, 14, and 16, 18 that are separated from each other by 2 cm to 4 cm, more preferably 2.5 cm to 3.5 cm, more preferably still by about 3 cm. The presence of these holes on each blade facilitates the placement of positioning devices with an applicator to the vaginal epithelium through the holes. Also, the speculum 10 provides for precise mapping of the modified POP-Q vaginal points in a very user friendly and easy manner. The speculum 10 includes a hymeneal line indicator 13, which is placed over the patient's hymeneal line. Hence, the proximal holes 12, 16 are 2 cm to 4 cm, more preferably 2.5 cm to 3.5 cm, more preferably still 3 cm distal to the hymeneal line 13, and therefore the examiner can place the Aa and Ba positioning devices through the proximal hole 16 and distal hole 18 of the anterior blade 19, respectively. In a similar manner, placement of the Ap and Bp positioning devices may be effectuated through the proximal hole 12 and distal hole of posterior blade 11, respectively. Distal blades may be located on the tip of each blade 11, 19 and used for the placement of positioning devices C and D.

Using the speculum 10 as a positioning tool, attachment of the positioning devices to the vaginal epithelium may be achieved with an adhesive material, grasping clips or with a stapling device, if needed. A preferred technique for placement of the positioning devices is as follows:

1) The patient is placed in dorsal lithotomy and a relaxed position. The vagina is prepped with alcohol (ETOH) in order to improve the attachment of the positioning devices. Then, with the use of the speculum 10, pelvic organ prolapse is reduced by the examiner, and the implantation of the positioning devices is performed as indicated in the following.

2) Positioning device C is placed on the anterior formix through the distal hole 18 of anterior blade 19.

3) Positioning device D is placed on the posterior formix through the distal hole 14 of posterior blade 11.

4) If the cervix is surgically absent then only positioning device C is placed on the leading edge of the vaginal cuff between anterior blade 19 and posterior blade 11.

5) The speculum 10 is pulled out gently until the hymeneal line 13 of the speculum 10, which may be marked in color such as red, is placed on the patient's hymeneal ring.

6) Positioning devices Aa and Ap are placed though the proximal anterior 19 and proximal posterior 12 holes, respectively.

7) Positioning devices Ba and Bp are placed though the distal anterior 18 and distal posterior 14 holes, respectively.

8) Speculum 10 is gently removed from the patient's vagina.

FIGS. 2, 3, 4 and 5 show the placement of various embodiment intra-vaginal positioning devices after completion of the above eight steps. Although any suitable positioning device and related positioning device receiver may be used, the following three specific embodiments respectively cover ultrasonic, RFID and electromagnetic sensor implementations for illustrative purposes.

FIG. 2 generally illustrates positioning devices placed on the vaginal epithelium according to the modified POP-Q mapping system described above. Also, a schematic depiction of the distances and spatial relationships between extracorporeal positioning device receivers and the intra-vaginal positioning devices is demonstrated from the sagital view. The patient is preferably in a relaxed condition with completely reduced pelvic organ prolapse to its presumed normal anatomy (which may be considered time zero of the test).

Figure 3:
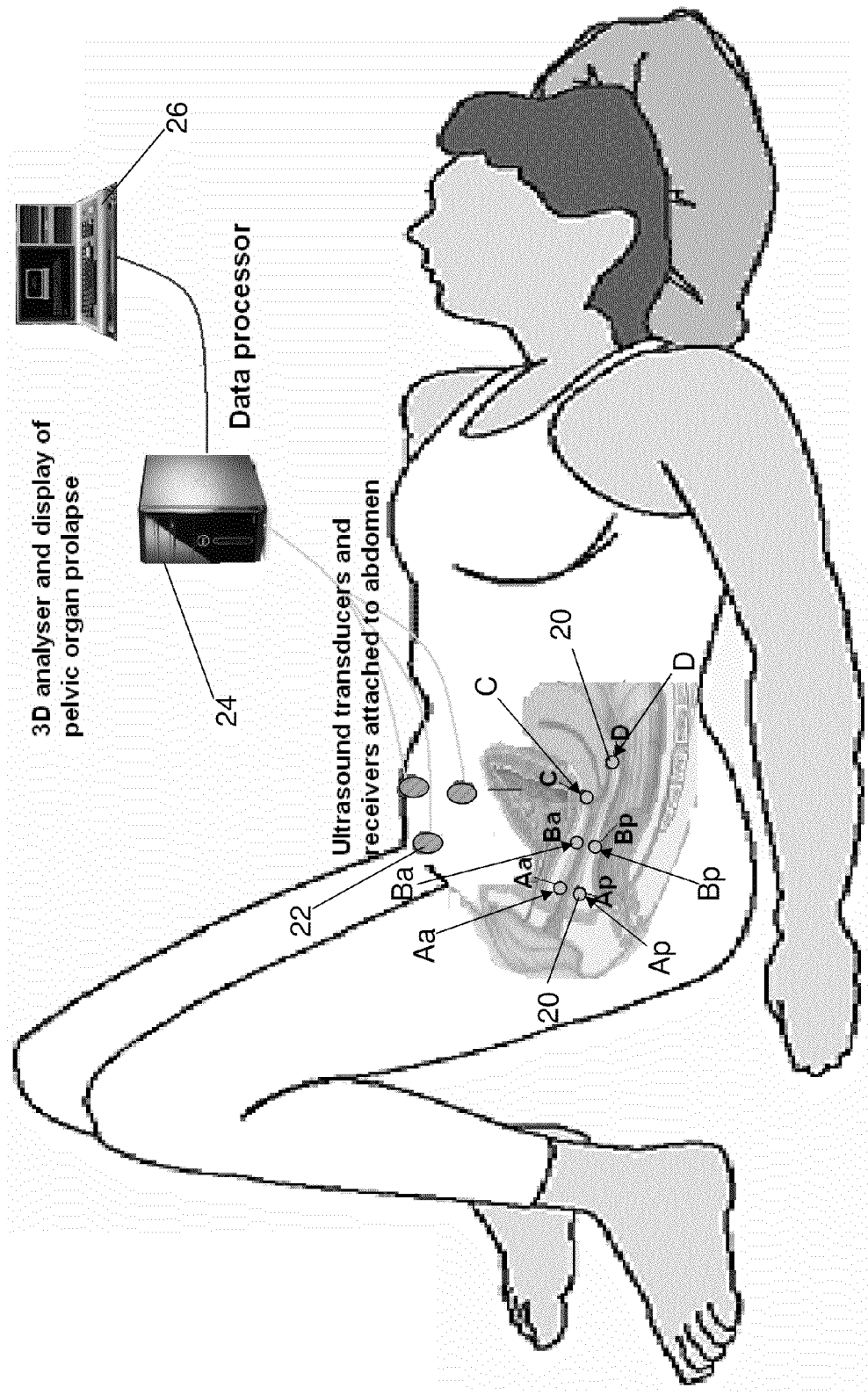
FIG. 3 a schematic depiction of distances and spatial relationships between extracorporeal (abdominal) ultrasound complex transducers/receivers and the intra-vaginal ultrasonic reflectors as demonstrated from a sagital view.

FIG. 3 is a schematic depiction of the distances and spatial relationships between extracorporeal (abdominal) specific embodiment ultrasound complex transducers/receivers 22 and the intra-vaginal ultrasonic reflectors 20 at positions Aa, Ba, Ap, Bp, C, D as demonstrated from the sagital view. Also, connection between the ultrasonic receivers 22 and the data processor/3D analyzer 24 and display 26 is shown. The patient is in a relaxed condition with completely reduced pelvic organ prolapse to its presumed normal anatomy (time zero of the test).

The ultrasound-based measuring system has three major components:

a) Multiple ultrasound transducers and receivers 22 that are located externally on the abdomen of the patient being examined.

b) As indicated above, multiple (such as three to six) small, preferably disposable acoustic signal reflectors 20 as positioning devices are attached internally inside the patient's vagina. In certain embodiments the sono-opacity, quality or both of the reflectors 20 are made different in order to make each reflector 20, and their respective reflecting signals, distinguishable from the others by the receiver 22. The placements of these signal reflectors 20 are in specific sites of the vagina as indicated in FIGS. 2 and 3 and described above in the modified POP-Q methodology. And, c) a microprocessor-based data processing and display unit 24, 26 located externally to the patient and attached to the ultrasound transducers and receivers 22, by means of a cable or with a wireless connection, as indicated in FIG. 3. It will be appreciated that although shown as separate devices, the processor 24 and analyzer and display 26 may be part of a single system, or may even be the same system.

Figure 4:
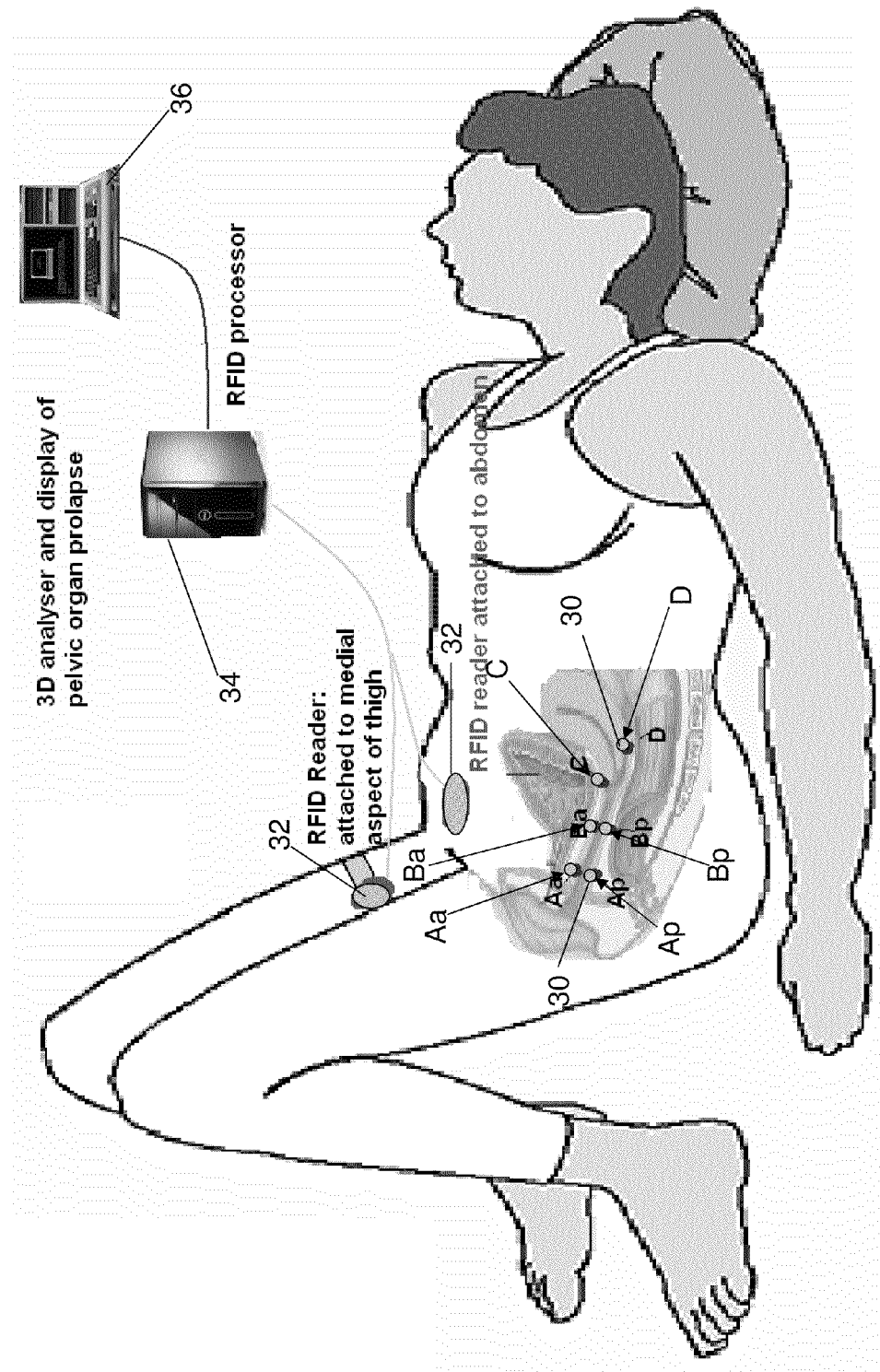
FIG. 4 a schematic depiction of the distances and spatial relationships between extracorporeal RFID readers and intra-vaginal RFID tags as demonstrated from a sagital view.

FIG. 4 a schematic depiction of the distances and spatial relationships between extracorporeal RFID readers 32 and the intra-vaginal RFID tags 30 at positions Aa, Ba, Ap, Bp, C, D, as demonstrated from the sagital view. Also, connection between the RFID readers 32 and the data processor 34 and 3D analyzer and display 36 is demonstrated. The patient is in a relaxed condition with completely reduced pelvic organ prolapse to its presumed normal anatomy (time zero of the test).

The radio-frequency identification (RFID)-based measuring device also has three major components:

a) Multiple (such as three to six) radio-frequency identification (RFID) tags 30, which are passive, preferably disposable, inexpensive, and tiny microchips that are coupled to an antenna, and which are attached internally inside the patient's vagina. The passive tags 30 are activated when within the response range of an RFID reader 32. The RFID reader 32, serving as the positioning receiver, emits a low-power radio wave field which is used to power the tags 30 so as to pass on any information that is contained on the chip within a tag 30. Each tag 30 reflects different signals, which makes it distinguishable from others by the reader 32. The RFID tags 30 may be encased in a special casing that does not irritate or react with the living tissues to which they are attached. The casing may be, for example, a biocompatible glass that is transparent to the scanning radio-frequency signal that activates the chip 30.

The placement positions of these RFID tags 30 are in the specific sites of the vagina indicated in FIGS. 2 and 4, and described above in reference to the modified POP-Q methodology.

b) A radio-frequency identification (RFID) reader 32 located on, for example, the abdomen or medial aspect of the patient's thigh. Other positions may also be possible, however, both in relation to or independent of the patient. Communication between the RFID reader 32 and the tags 30 occurs wirelessly and generally does not require a line of sight between the devices 30, 32. A radio-frequency identification (RFID) reader 32 contains a module (transmitter and receiver), a control unit and a coupling element (antenna). The reader 32 has three main functions: energizing of the tags 30, demodulating the signals received from the tags 30 and decoding of the demodulated signal. In addition, readers 32 can be fitted with an additional interface that converts the radio waves returned from the RFID tag 30 into a form that can then be passed on to another system, like a computer or any programmable logic controller 34, 36. The reader 32, or a combination of readers 32, may then determine the locations of the tags 30 using known techniques. Anti-collision algorithms permit the simultaneous reading of large numbers of tagged objects, while ensuring that each tag 30 is read only once.

c) A microprocessor-based data processing and display unit 34, 36 located externally to the patient and attached to the RFID reader 32, by means of a cable or with a wireless connection, as indicated in FIG. 4.

Figure 5:
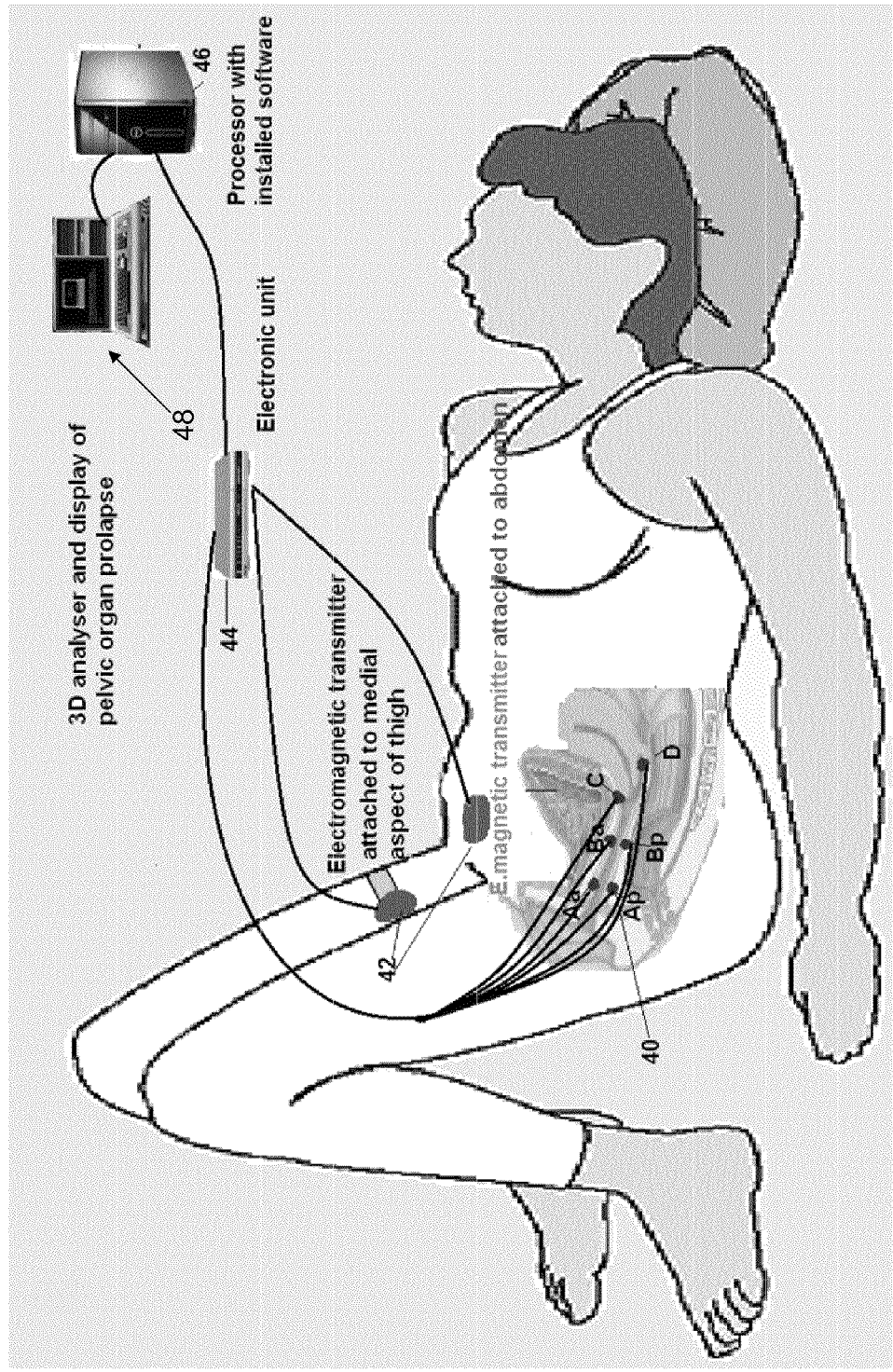
FIG. 5 a schematic depiction of the distances and spatial relationships between an extracorporeal electromagnetic transmitter/receiver and intra-vaginal electromagnetic sensors as demonstrated from a sagital view.

FIG. 5 a schematic depiction of the distances and spatial relationships between an extracorporeal electromagnetic transmitter 42, serving as a portion of a positioning receiver, and intra-vaginal electromagnetic micro-sensors 40, serving as positioning devices, at positions Aa, Ba, Ap, Bp, C, D, as demonstrated from the sagital view. Also, connection between the electromagnetic transmitter 42 and the electronics unit 44, which together may serve as the positioning receiver, and 3D analyzer and display 46 is demonstrated. The patient is in a relaxed condition with completely reduced pelvic organ prolapse to its presumed normal anatomy (time zero of the test).

In various embodiments, an electromagnetic-based tracking device 42 is a high-accuracy electromagnetic tracker designed for short-range motion tracking applications. It may employ pulsed DC technology to track the position and orientation (six degrees-of-freedom or 6DOF) of multiple intra vaginal sensors 40 within the operating range of the transmitter 42. Sensor data may be reported serially to a host computer via a USB or RS232 interface, for example. An example of such a device is the 3D Guidance trakSTAR by Ascension Technology Corporation, Burlington Vt.

The electromagnetic-based tracking device 42 determines six degrees-of-freedom (6DOF) of the position and orientation (X, Y, Z, Azimuth, Elevation, and Roll) of one or more intravaginal sensors 40 referenced to a fixed extracorporeal transmitter 42. The transmitter 42 sequentially generates magnetic fields and each sensor 40 instantly measures the transmitted field vectors at a point in space. From theoretical knowledge of the transmitted field, each tracking device 40 accurately deduces the real-time location of the devices 40 relative to the transmitter 42.

The electromagnetic-based tracking system 40, 42 may have the following components:

a) Multiple (such as three to six) electromagnetic micro-sensors 40, providing a tracking solution that includes the position in three dimensions and the orientation of the three sensor 40 axes relative to the tracking system's reference frame, which may be determined by the transmitter 42. 6DOF sensors 40 may be factory-calibrated and the calibration data may be stored on a memory chip in the sensor's 40 connector housing. The electromagnetic micro-sensors 40 are attached internally inside the patient's vagina, as, for example, described above. The transmitter 42 sequentially generates magnetic fields and each sensor 40 generates corresponding positioning information based upon the magnetic field. The sensors 40 may be attached to the vaginal epithelium with a non-metallic clipper or with stickers, for example. The intra-vaginal micro-sensors 40 may be electrically and communicatively connected to the electronic unit 42 with wire; however a wireless connection is also possible between sensor 40 and electronic unit 42.

The placement positions of these electromagnetic micro-sensors 40 are preferably in the specific sites of the vagina indicated in FIGS. 2 and 5, and described above in reference to the modified POP-Q methodology.

b) An electromagnetic transmitter 42 located, for example, on the abdomen or medial aspect of the patient's thigh, or attached to the exam table; of course, other positions may be possible. The transmitter 42 may include a high permeability core with three concentric sets of coils, each coil having an axis at right angles to the other two. Magnetic fields along the X, Y, and Z axes of the transmitter 42 are created when current flows in their respective windings. The strength of the magnetic field is highest near the transmitter 42 and falls off with the inverse cube of the distance from the transmitter 42. The transmitted field of a given axis may have, for example, a trapezoidal magnitude characteristic as a function of time. Each of the three coils is sequentially energized in this manner during each measurement cycle. The transmitter 42 may also include an electronics unit that is used to compute tracking solutions, sensor signal processing, as well as provide power conditioning and host interface functions; the electronics unit 44 may be packaged in a desktop enclosure with a built-in power supply.

The transmitter drive circuitry may include a precision current source, with a maximum output of, for example, 3.0 A. The electronics unit 44 may detect the absence of a transmitter 42 by monitoring the current. If current is interrupted, the transmit driver 44 may turn off until a valid transmitter 42 is detected. This ensures that the connector to the transmitter 42 is de-energized when open. Also, the transmitter 42 may be fault-protected for ground shorts. In the event of a short to ground on any wire from the tracker 40 to the electronics unit 44, or from the electronics unit 44 to the transmitter 42, no damage will result to the trackers 40 and no excessive current hazard conditions will occur.

The sensor signal processing circuitry 44 may acquire the signals from the sensors 40 for each of the transmitter 42 coils and continuously convert these signals to corresponding digital values during the entire transmitter 42 axis time (i.e., time when that transmitter axis is energized). This input digital value may summed in an accumulator (i.e., a digital integrator) and the final value output and used to generate positioning information. As noted above, the sensor 40 connectors may be fault protected for ground shorts; hence, preferably no damage to the system or excessive current hazards will result from the shorting any sensor 40 connector pin or wire to ground.

The electronics unit 44 may employ, for example, two onboard processors. A first processor may handle all communications to and from a host device, such as a PC 46. It may also compute the tracking solutions for the transmitter 42. A second processor may perform all acquisition and digital signal processing of the sensor data. For a measurement cycle, the tracking system may activate transmitter 42 coils sequentially and produces a data record (i.e. full tracking solution) following each coil measurement. Once each transmitter 42 coil has been activated, a system measurement cycle is complete and a new cycle begins. Thus, a dipole (3-coil) transmitter 42 running at a measurement rate of 50 Hz will compute 150 tracking solutions per second.

It will be appreciated that other types of positioning devices and related external equipment may be used; the above specific embodiments are merely exemplary in nature.

The Modified POP-Q Methodology in Use

The following steps set forth a preferred embodiment modified POP-Q method with respect to the above three embodiment systems. It will be appreciated, however, that this methodology may be employed using any suitable position measuring system.

1) Positioning of the subject: The patient is placed in the dorsal lithotomy position.

2) Preparation: The vagina is prepped with ETOH in order to improve the attachment of the positioning devices, such as magnetic sensors 40, tags 30 or reflectors 20.

3) Multiple ultrasound transducers and receivers 22 (usually three of each, but more are possible) or at least one RFID reader 32, or electromagnetic transmitter 42 are attached externally on the abdomen or on the medial side of the thigh of the patient being examined, as shown in FIGS. 2-4, or placed near the patient, such as on an examination table, affixed to a wall, etc.

4) Using the speculum 10 for the test, the pelvic organ prolapse is reduced by the examiner, and the positioning devices 20, 30, 40 are placed on the previously described points C, D, Aa, Ba, Ap, Bp. Attachment of the positioning devices 20, 30, to the vaginal epithelium may be achieved with an adhesive material, with a stapling device if needed, or by any other suitable means.

In preferred embodiments the active components of the positioning system (i.e., the active ultrasound 22 or RFID transmitting component 32, or electromagnetic transmitter 42) are extracorporeal, whereas the positioning devices, such as the reflectors 20, tags 30 or sensors 40, are located internally and are very light and small. These devices are therefore comfortable for the patient. In the case of ultrasound and RFID based devices, as the internally located components are passive, and do not actively transmit energy (acoustic, radio-frequency, etc.), these passive devices may be very cheap and therefore disposable. This decreases the potential risk of transmitting any infection to the patient by using totally sterile and disposable positioning devices. However, it will be appreciated that active positioning devices may be used for other embodiment systems such as the electromagnetic sensors 40. For example, with regards to an electromagnetic tracking system, the sensor(s) 40 placed intravaginaly are active and may or may not be disposable.

5) The examiner measures the genital hiatus (gh), the perineal body (pb), and the total vaginal length (TVL), and all measured numbers are entered into the computer 24, 34, and 46 for future processing of the data and diagnostic purposes.

6) The patient in the relaxed condition, after complete reduction of pelvic organ prolapse, is placed in the trendelenburg position.

7) The positioning system is activated, and the active components of the positioning system (such as the ultrasound transducers 22, RFID receivers 32 or electromagnetic transmitter 42) identify the passive components (such as the reflectors 20, tags 30 or magnetic sensors 40) located inside the patient's vagina. For example, in the electromagnetic tracking system, the transmitter 42 sequentially generates magnetic fields and the sensors 40 instantly measure the transmitted field vectors at their respective points in space from which the system deduces the real-time location of the sensor(s) 40 relative to the transmitter 42.

With specific respect to the ultrasound-based embodiment, the extracorporeal ultrasound transducers 22 transmit ultrasonic signals into the body of the patient. The ultrasonic signals are received by the small, preferably disposable signal reflectors 20 that are attached to the vaginal epithelium, and reflected back to the extracorporeal receiver 22. These echogenic signal reflectors 20 may include inorganic materials such as small water bags, steel, plastic, etc, with different sono-opacity and are referred to hereinafter as "inorganic ultrasound reflectors" so as to differentiate them from organic ultrasound reflectors, such as the patient's tissues and organs, which are also encountered by the transmitted ultrasonic acoustic signals. The extracorporeal ultrasonic receivers 22 may thus identify each reflector 20 based on their respective sono-opacity characteristics.

With specific respect to the RFID-based embodiments, the RFID receiver unit 32 may measure the distances between the RFID tags 30 based upon a time delay calculation. The RFID positioning system bases distance calculations on the delay time of the electromagnetic (EM) waves used in the communications between reader/writers (antennas) 32 and the RFID tags 30. This enables highly accurate distance estimations for UHF-band EPC-compliant tags, which are currently the most widely used tags. Like sound, electromagnetic waves take longer to reach a target the further away it is. As a result, the time taken for the EM waves to travel from an antenna 32 to an RFID tag 30 and return again (the "delay time") differs according to the distance between the two points 30, 32. The direction a tag 30 is facing has no effect on the delay time and thus does not compromise the measurement accuracy. Furthermore, each RFID tag 30 located at a specific location on the vaginal epithelium may be identified separately by the reader 32 and the distance of each tag 30 from the reader 32 may therefore be measured separately. Known spatial acquisition methods may be employed by the reader(s) 32 to determine the respective locations in 3-space of each tag 30, or the relative positions of the tags 30 with respect to each other.

With specific respect to the electromagnetic embodiments, the transmitter 42 sequentially generates magnetic fields and the sensors 40 measure the transmitted field vectors at their respective points in space, from which the real-time location of the sensor(s) 40 relative to the transmitter 42 may be deduced. The tracking system activates transmitter 42 coils sequentially and produces a data record (i.e. full tracking solution) following each coil measurement.

8) After completion of the identification process, by pressing on a "zero all" button or the like on the computing device 24, 34, 44, 46 the positioning system is set into a zero point condition with respect to any potential future movement of the positioning devices 20, 30, 40 as measured from their previously fixed and immobile positioning receivers.

9) The patient's position is changed by reversing the trendelenburg position, and the movement of each positioning sensor 20, 30, 40 is measured by the corresponding receiver system 22, 32, 42, 44.

The patient is then asked to strain or push down (the valsalva maneuver) and ultimately is asked to stand up.

The dislocation of each positioning device from its corresponding zero point position is measured with the same technology described above in step 7.

For example, in the embodiment employing ultrasound technology, the reflector 20 located at point Aa of the vaginal epithelium is identified by at least one ultrasound receiver 22. The location of the reflector 20 located at Aa, in comparison to other pelvic structures (like pelvic bone) will be reported to the processor 24 and this location will be marked and registered in the memory of the processor 24 at "time zero". After the performance of the valsalva maneuver by the patient, the Aa reflector 20 may be dislocated. The ultrasound receiver 22, will report the new location of the Aa reflector 20 to the processor 24. The Aa reflector 20 will be marked and registered in the memory of processor 24 as "post valsalva" or the like. Therefore, the processor 24 is able to measure the linear distance moved by the Aa reflector 20 by simply measuring the distance between the previously marked "time zero" and the newly marked "post valsalva" positions.

Embodiments employing RFID technology or electromagnetic technology may work with exactly the same concept. For example, the Ap RFID tag 30 may be identified by all of the readers 32 and its distance from each reader 32 may be measured at the "time zero" point. The location of the Ap RFID at "time zero" will be reported to processor 34 and will be marked and registered in its memory. Then, after any maneuver by the patient (for example after standing, etc.), the Ap RFID tag 30 may be dislocated because of patient pelvic prolapse, and therefore the new distance of the Ap tag 30 from each reader 32 will be reported to processor 34. The processor 34 will determine a new location for the Ap RFID tag 30 as a "post valsalva" location, by combining the data received from all readers 32. Processor 34 then will be able to measure the distance between the previously marked "time zero" and newly marked "post valsalva" positions.

These measurements may be performed for each positioning device independently, and may be performed serially or simultaneously by the receiver equipment. In preferred embodiments each positioning device is individually identifiable, as discussed above. However, it will be appreciated that in some embodiments the positioning devices may not be uniquely identifiable; however, the identification of each positioning device may be obtained by way of its location with respect to the patient, with respect to other positioning devices, or both.

The embodiment employing electromagnetic technology may work using the same concept. For example, at "Time Zero" after turning the machine (tracking system) on, the transmitter 42 sequentially generates magnetic fields and the Ap sensor 40 instantly measures the transmitted field vectors at a point in space, within the operating range of the transmitter 42. The tracking system activates transmitter 42 coils sequentially and produces a data record (i.e. full tracking solution) following each coil measurement. Once each transmitter 42 coil has been activated, a system measurement cycle is complete and a new cycle begins. Thus, a dipole (3-coil) transmitter 42 running at a measurement rate of 50 Hz will compute 150 tracking solutions per second.

The Ap sensor 40 data may be reported serially to the electronic unit 44 via a USB or RS232 interface, or wirelessly. These data are ultimately transferred to a host computer 46 for analysis. The electromagnetic-based tracking device 44 determines six degrees-of-freedom (6DOF) positions and orientations (X, Y, Z, Azimuth, Elevation, and Roll) of the Ap sensor 40 (and other sensors 40) referenced to the fixed extracorporeal transmitter 42. From theoretical knowledge of the transmitted magnetic field, the electronic unit 44 accurately deduces the real-time locations of the positioning devices 40 relative to the transmitter 42.

The location of the Ap sensor 40 at "time zero" may be reported to processor 46 and marked and registered in the memory of the processing unit 46. Then, after any maneuver by the patient (for example after valsalva, standing, etc.), the Ap sensor 40 may be dislocated because of patient pelvic prolapse, and therefore the new distance of the Ap sensor 40 from transmitter 42 will be reported to processor 46 via electronic unit 44. The processor 46 may determine a new location for the Ap sensor 40 as a "post valsalva" location, by deducing the new real-time location of the sensor 40 relative to the transmitter 42. Processor 46 may then measure the distance between the previously marked "time zero" and newly marked "post valsalva" positions. These measurements may be performed for each positioning device 40 independently, referenced to the fixed extracorporeal transmitter 42.

Different prolapse conditions in a patient can be determined by the final positions of the positioning devices. For example, FIG. 6 illustrates the displacement of positioning devices 20, 30, 40 after a valsalva maneuver performed by a patient suffering from "uterine prolapse." FIG. 7 illustrates the displacement of positioning devices 20, 30, 40 after a valsalva maneuver performed by a patient suffering from "Cystocele." FIG. 8 illustrates displacement of positioning devices 20, 30, 40 after a valsalva maneuver performed by a patient suffering from "Rectocele."

With regards to the embodiments discussed above, the respective data processing and display units may receive positioning information from the positioning devices and positioning receivers and process this information to determine the location of each positioning device within the patient, or the relative locations of the positioning devices with respect to each other. This information in addition to, for example, data entered by the examiner regarding total vaginal length (TVL), and length of the perineal body (pb), will enable the software of processor 24, 34, 46 to reproduce a 2D OR 3D image of the patient's pelvis at "time zero" (prolapse is reduced and patient is relaxed, as indicated in the figures). After receiving positioning data about the dislocation of each positioning device, this positioning data is processed in the computer 24, 34, 46 and software within the computer 24, 34, 46 creates a two or three dimensional image from the examined patient's pelvic area and the degree of the defects (prolapse) after each maneuver. Creation of such software should be routine for one of ordinary skill in the art after having the benefits of the instant disclosure. As known in the art, such software may be stored in the memory of the computer system 24, 34, 46 and be executable by one or more processors in the system 24 to perform various logical steps to generate the desired output discussed above based upon the input positioning information and, optionally, other patient-related data entered by a user of the system. Such software may include data relating generally to patient anatomy, configuration information related to the particular positioning receiver and devices being employed, calibration data for the positioning receiver, user input/output interfaces for the entry of test data, configuration data and calibration data; mapping software to visually and numerically indicate the positions, movements or both of the positioning devices based upon the received positioning information and the patient anatomy, and diagnostic algorithms that employ the positioning information to provide a potential diagnosis.

Figure 7:
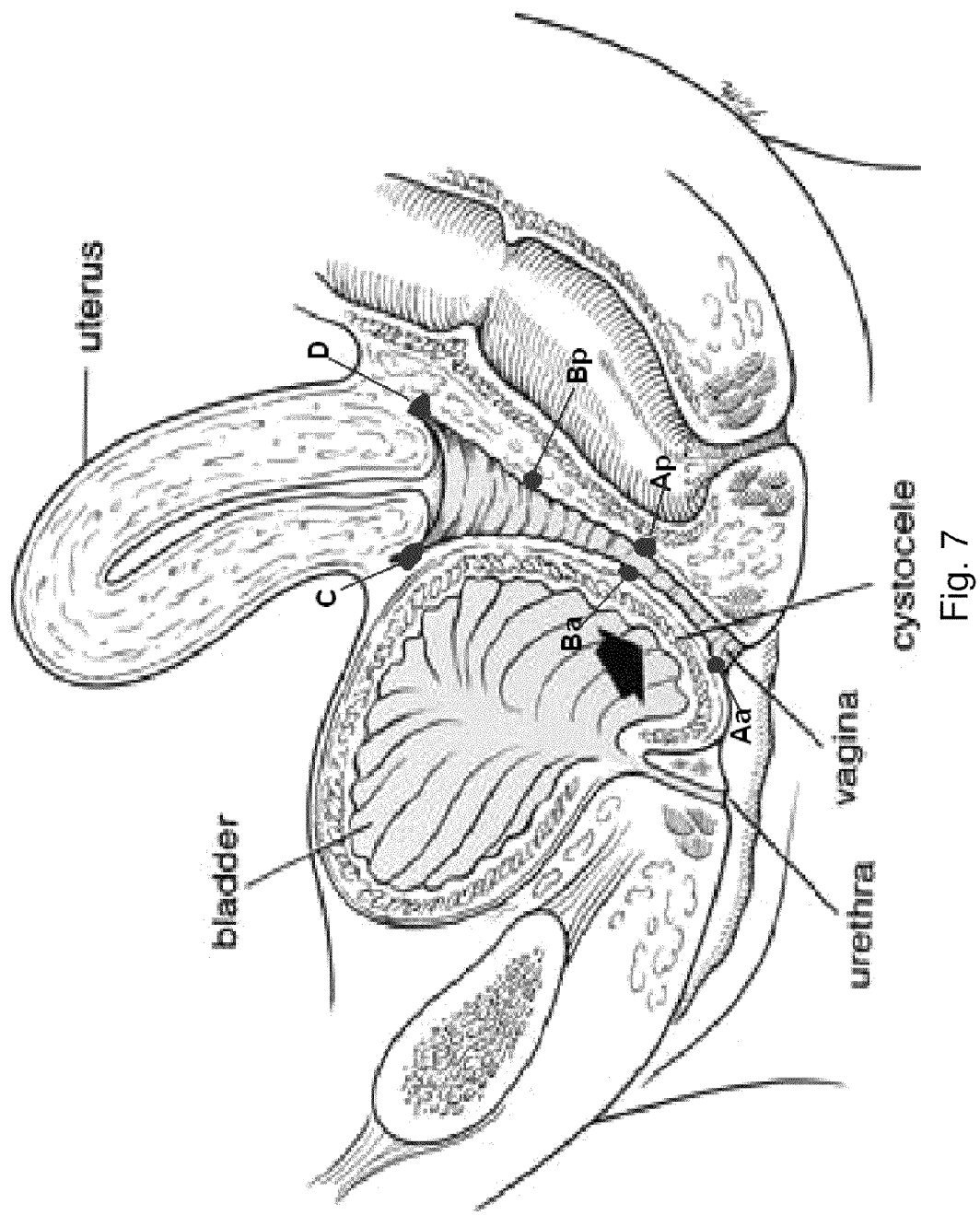
FIG. 7 illustrates displacement of positioning devices after a valsalva maneuver performed by a patient suffering from "Cystocele."

For example, in a patient X, the "time zero" image shown in FIG. 7 is processed by the processing equipment 24, 34, 46 and presented on a display 26, 36, 48. After the valsalva maneuver, the positioning devices 20, 30, 40 located at points C, D, Ap, and Bp may not show any dislocation. However the positioning devices located at Aa and Ba may have moved 3 cm and 2 cm, respectively. The software executed by the processor(s) within the system 24, 34, 46 may cause the processors to control display circuitry to reproduce the image shown in FIG. 7 on the display 26, 36, 48, which is consistent with a diagnosis for Cystocele. This image may be shown on display 26, 36, 48 as a 2D or 3D image, for example. This "post valsalva" image, along with the "time zero" image, may be recorded and saved or printed for the patient medical records.

Figure 6:
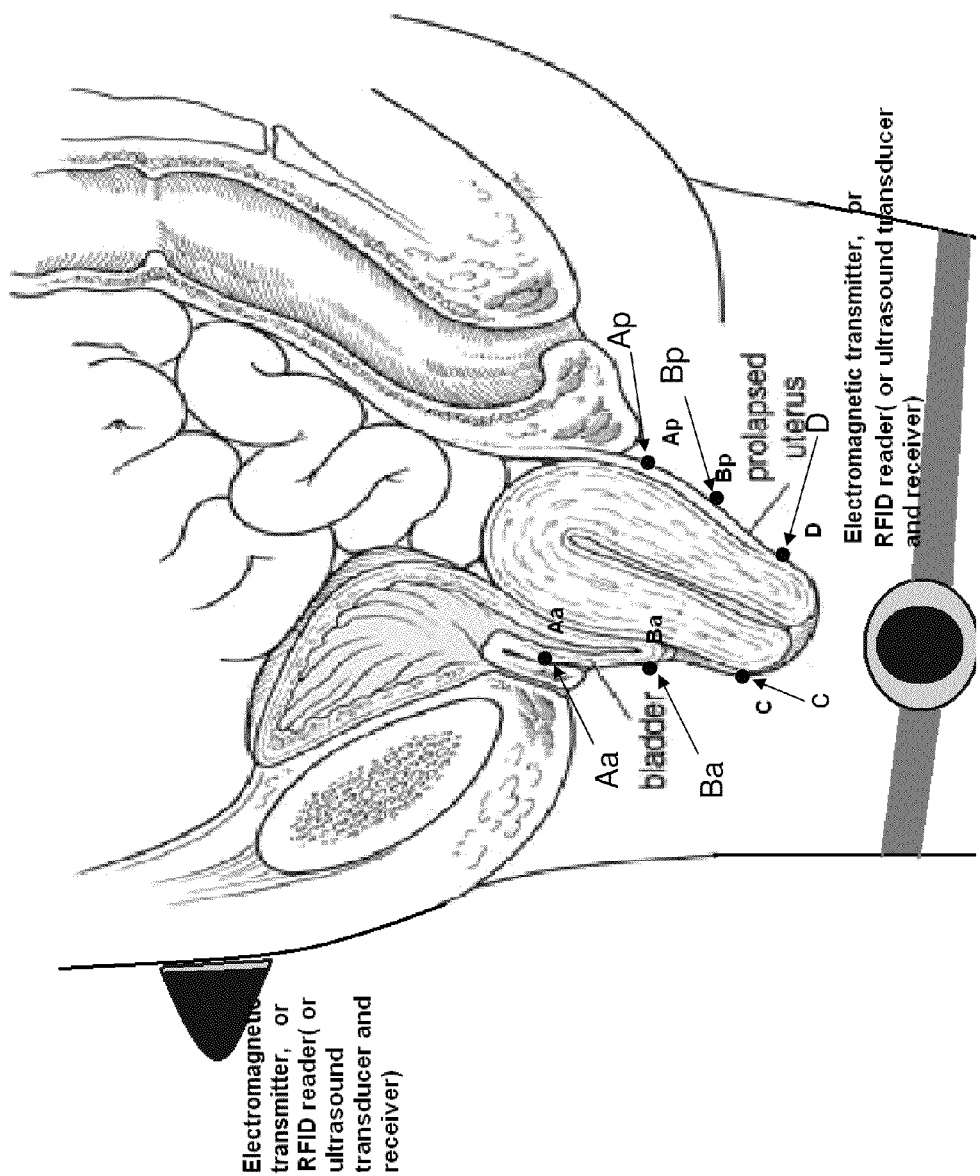
FIG. 6 illustrates displacement of positioning devices after a valsalva maneuver performed by a patient suffering from "uterine prolapse."
Figure 8:
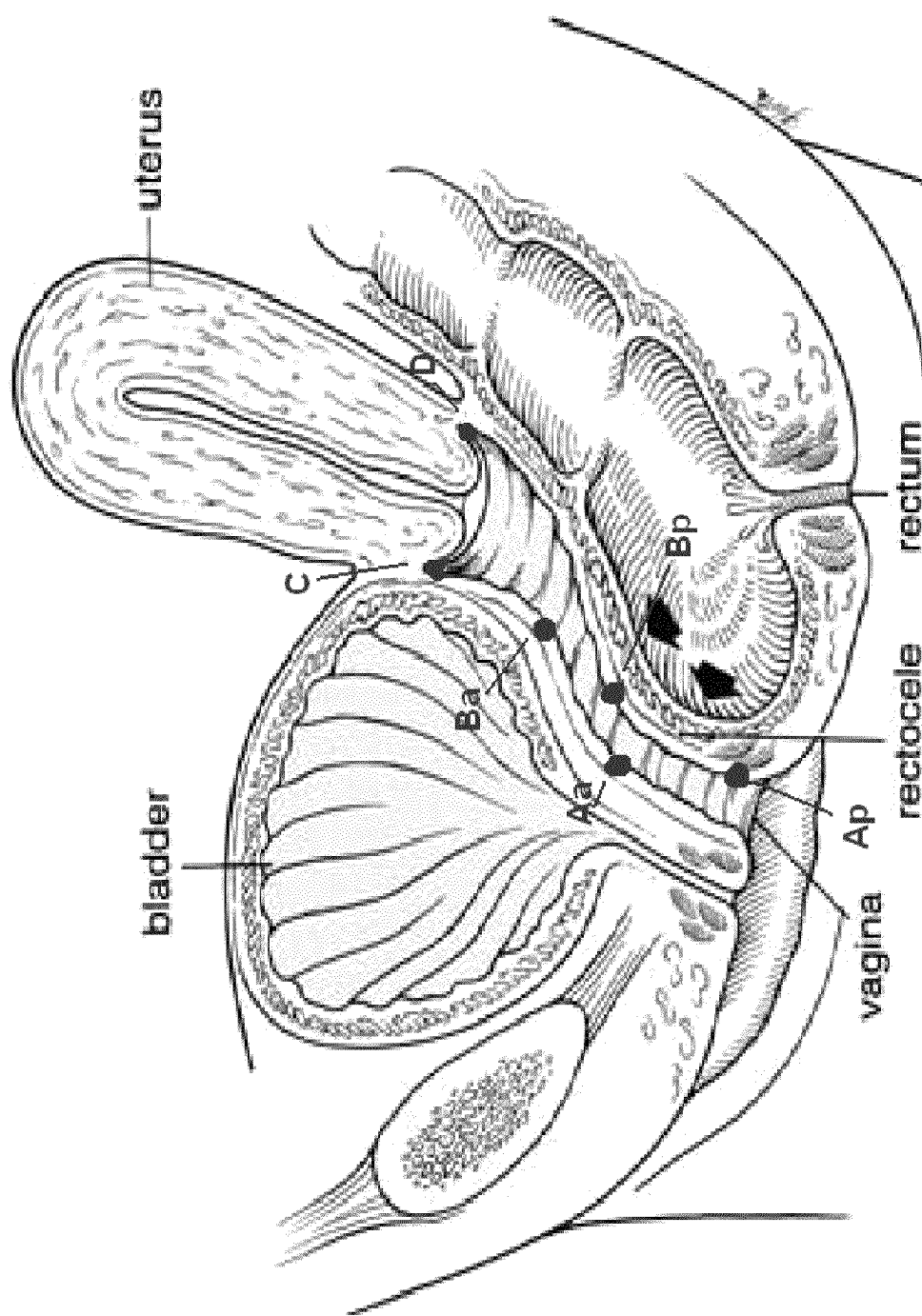
FIG. 8 illustrates displacement of positioning devices after a valsalva maneuver performed by a patient suffering from "Rectocele."
Figure 9:
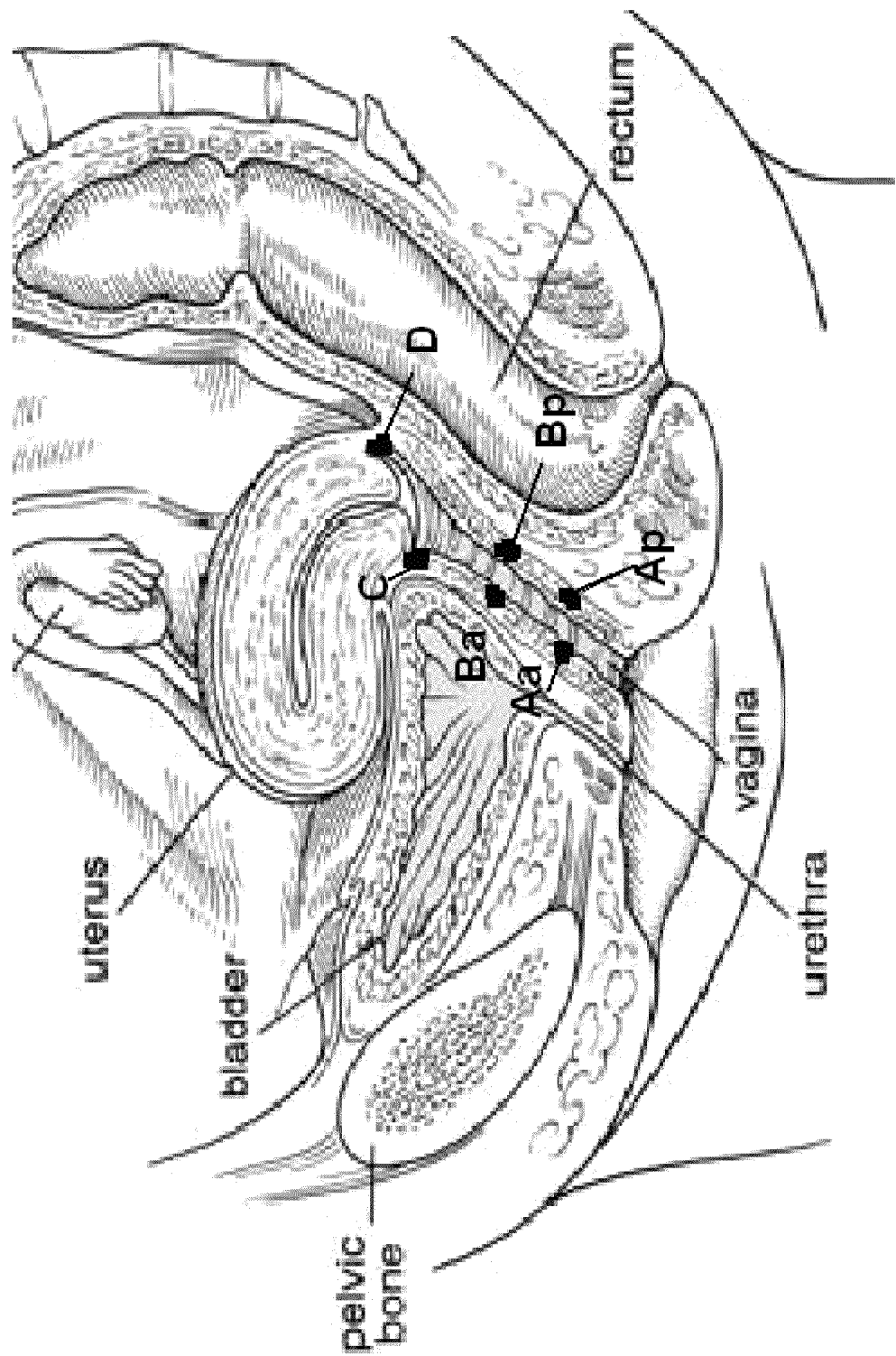
FIG. 9 illustrates the normal position of pelvic organs.

As indicated in FIGS. 6 to 8, at least three different types of pelvic organ prolapse may be diagnosed by the computer 24, 34, 46 based upon different levels of dislocation of the positioning devices 20, 30, 40. Information indicative of the position, location, movement or a combination thereof of the positioning devices 20, 30, 40 may be presented visually, numerically or both upon display 26, 36, 48 controlled by the computer 24, 34, 46. The software may also present a suggested diagnosis based upon the relative positions and movement of the positioning devices 20, 30, 40.

The software installed in the computer 24, 34, 46 may be coded to be capable of accurately and site-specifically describing, quantifying, and staging pelvic defect and prolapse in women in order to provide a standardized means for documenting, comparing, and communicating clinical findings with proven interobserver and intraobserver reliability. The computer 24, 34, 46 may also be capable of creating three dimensional (3D) or two dimensional images of female pelvic anatomy on the display 26, 36, 48 without any need for harmful radiation (in contrast to MRI or CT scans, etc.). Embodiment positioning systems also provide a tool for monitoring the degree of prolapse before and after any reconstructive surgery, and also for prolonged postoperative monitoring of the pelvic support. This may help to precisely identify any possible failure of the surgical treatment. Hence, various embodiments provide a precise pelvic organ prolapse measurement tool for research purposes, as well as for comparing different reconstructive surgical techniques and their respective failure rates over time.

All publications cited in the specification, both patent publications and non-patent publications, are indicative of the level of skill of those skilled in the art to which this invention pertains. All these publications are herein fully incorporated by reference to the same extent as if each individual publication were specifically and individually indicated as being incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the following claims.

What is claimed is:

1. A method for measuring pelvic organ prolapse comprising:
   a) attaching a plurality of positioning sensors to an internal surface of a vaginal cavity of a subject at predetermined locations within the vaginal cavity whereby the sensors are attached to the surface;
   b) utilizing the positioning sensors to obtain first position-related information while the subject is in a first position;
   c) instructing the subject to perform a movement adapted to cause displacement of at least one of the positioning sensors;
   d) utilizing the positioning sensors to obtain second position-related information; and
   e) determining at least a characteristic of pelvic organ prolapse utilizing the first position-related information and the second position-related information, wherein the determining step is performed by a computing system operative to receive the first position-related information and the second position-related information and to compute movement of the plurality of positioning sensors located within the vaginal cavity.

2. The method of claim 1 wherein disposing the plurality of positioning sensors at predetermined locations within the vaginal cavity comprises attaching each positioning sensor to a corresponding internal surface of the vaginal cavity.

3. The method of claim 1 wherein the first position is a relaxed position.

4. The method of claim 1, wherein the plurality of positioning sensors are at least two positioning sensors.

5. The method of claim 1, wherein the first position-related information and the second position-related information is received by at least one extracorporeal positioning receiver that is located at a fixed position.

6. The method of claim 1, wherein the plurality of positioning sensors are attached to the internal surface via an adhesive material, a grasping clip, a clamp, or a stapling device.

7. The method of claim 1, wherein the positioning sensors are selected from the group consisting of electromagnetic sensors, RFID tags, and ultrasonic reflectors.

8. The method of claim 1, wherein the first position-related information and second position-related information are obtained using a tracking device that comprises at least one extracorporeal transmitter for generating a predetermined magnetic, RFID, or ultrasound field.

* * * * *